(12) United States Patent
Cao et al.

(10) Patent No.: US 12,085,547 B2
(45) Date of Patent: Sep. 10, 2024

(54) BUFFER ASSEMBLY FOR DEVICE FOR ANALYZING NOBLE GAS ISOTOPE IN NATURAL GAS AND NOBLE GAS ISOTOPE ANALYSIS METHOD

(71) Applicant: NORTHWEST INSTITUTE OF ECO-ENVIRONMENT AND RESOURCES, CAS, Lanzhou (CN)

(72) Inventors: Chunhui Cao, Lanzhou (CN); Liwu Li, Lanzhou (CN); Huanhuan Zhao, Lanzhou (CN)

(73) Assignee: NORTHWEST INSTITUTE OF ECO-ENVIRONMENT AND RESOURCES, CAS, Lanzhou (CN)

( * ) Notice: Subject to any disclaimer, the term of this patent is extended or adjusted under 35 U.S.C. 154(b) by 0 days.

(21) Appl. No.: 18/389,671

(22) Filed: Dec. 19, 2023

(65) Prior Publication Data

US 2024/0118255 A1   Apr. 11, 2024

(30) Foreign Application Priority Data

Mar. 10, 2023   (CN) .......................... 202310229515.8

(51) Int. Cl.
  *G01N 33/00*    (2006.01)
  *G01N 1/22*     (2006.01)
  *G01N 1/28*     (2006.01)

(52) U.S. Cl.
  CPC ................................. *G01N 33/0036* (2013.01)

(58) Field of Classification Search
  CPC ........ G01N 33/0036; G01N 1/28; G01N 1/22; Y10T 137/1026; Y10T 137/218; Y10T 137/1153; B01L 3/502738; B01L 3/50273; B01L 3/502746; B01L 2400/08; B01L 2400/082; B01L 2400/084; F15D 1/001; F15D 1/02; F15D 1/025; F15D 1/00

See application file for complete search history.

(56) References Cited

U.S. PATENT DOCUMENTS

| | | | |
|---|---|---|---|
| 3,521,493 A | 7/1970 | Pannetier et al. | |
| 6,588,545 B1 * | 7/2003 | Lee .......................... | F01N 1/088 181/279 |
| 2005/0256646 A1 | 11/2005 | Ellis | |

FOREIGN PATENT DOCUMENTS

| | | | | |
|---|---|---|---|---|
| CN | 107167510 B | 8/2020 | | |
| CN | 113252421 A | 8/2021 | | |
| CN | 113339703 A | * | 9/2021 | ............... F17D 1/04 |
| GB | 1355606 A | 6/1974 | | |
| WO | 9723779 A1 | 7/1997 | | |

* cited by examiner

*Primary Examiner* — Peter J Macchiarolo
*Assistant Examiner* — Anthony W Menga Fuentes

(57) ABSTRACT

A buffer assembly for a noble gas isotope analysis device, including an air inlet pipe and an air-pressure buffer member. The air inlet pipe is connected to the noble gas isotope analysis device, and is provided with a valve. The air-pressure buffer member is provided in the air inlet pipe, and includes a connecting pipe arranged inside the air inlet pipe. Multiple pneumatic components are sleeved outside the connecting pipe, and are configured to be deformed under the action of a gas flow to decelerate the gas flow. A noble gas isotope analysis device including the buffer assembly and an isotope analysis method using the noble gas isotope analysis device are also provided.

4 Claims, 9 Drawing Sheets

BUFFER ASSEMBLY FOR DEVICE FOR ANALYZING NOBLE GAS ISOTOPE IN NATURAL GAS AND NOBLE GAS ISOTOPE ANALYSIS METHOD

CROSS-REFERENCE TO RELATED APPLICATIONS

This application claims the benefit of priority from Chinese Patent Application No. 202310229515.8, filed on Mar. 10, 2023. The content of the aforementioned application, including any intervening amendments thereto, is incorporated herein by reference in its entirety.

TECHNICAL FIELD

This application relates to noble gas analysis, and more particularly to a buffer assembly for a device for analyzing a noble gas isotope in natural gas and a noble gas isotope analysis method.

BACKGROUND

Noble gases have been extensively used as important tracers in the analysis of geological objects and geological processes due to their excellent chemical inactivity and low abundance. Noble gases are colorless, odorless, and tasteless, and have low melting and boiling points. They can be liquefied at low temperatures. In this regard, in the prior art, the noble gases are extracted from air (or other gas mixtures such as natural gas) mainly by liquefaction and fractionation.

Chinese patent No. 107167510B provides a method and device for analyzing Xe isotopes in methane-rich natural gas. The method includes steps of vacuum extraction of external natural gas, dehydration, low-temperature collection, Xe enrichment and isotope analysis, in which a plurality of valves and a vacuum extraction device are employed to separate Xe from the methane-rich natural gas for isotope analysis, so as to obtain isotopic information of Xe. The method and device have simple operation and high efficiency.

There are a great variety of noble gases including helium (He), neon (Ne), argon (Ar), krypton (Kr), xenon (Xe), where Krypton gas is colorless and odorless, and has been widely used in the electronics industry, electric light source industry, gas lasers and plasma jet technique. Kr isotopes include $^{78}$Kr, $^{80}$Kr, $^{82}$Kr, $^{83}$Kr, and $^{84}$Kr. Kr isotopes can be applied in the detection of surface, and are commonly used as a tracer.

Chinese patent No. 107167510B discloses a step to simultaneously collect the xenon component and the krypton component during the separation and concentration of xenon gas. In this patent, the device is connected to a methane-rich natural gas pipe, and a natural gas sample is extracted under negative pressure. There is large pressure variation at the connection between the natural gas pipe and a port of the valve V0, and the connection also suffers large impact from the natural gas, which may easily break the connection and cause the natural gas leakage. Therefore, it is necessary to introduce a component that can buffer changes of air pressure, so as to alleviate the impact of natural gas samples on the port of the valve V0.

SUMMARY

In order to solve the above technical problems, the present disclosure provides a buffer assembly for a device for analyzing a noble gas isotope in natural gas, which can buffer pressure changes, so as to reduce the impact of natural gas sample on a port of the valve V0.

An object of the present disclosure is to provide a buffer assembly for a device for analyzing a noble gas isotope in natural gas, comprising:
an air inlet pipe; and
an air-pressure buffer member;
wherein the air inlet pipe is connected to the noble gas isotope analysis device; the air inlet pipe is provided with a valve V0; and the air-pressure buffer member is arranged in the air inlet pipe;
the air-pressure buffer member comprises a connecting pipe; the connecting pipe is provided in the air inlet pipe; a plurality of pneumatic components are sleevedly provided outside the connecting pipe; and the plurality of pneumatic components are configured to be deformed under the action of a gas flow to slow down the gas flow.

In an embodiment, the connecting pipe is connected with an inner wall of the air inlet pipe through a supporting rod.

In an embodiment, each of the plurality of pneumatic components comprises a fixed ring; the fixed ring is fixedly provided on the connecting pipe; a movable ring is provided upstream of the fixed ring, and is movably sleeved outside the connecting pipe; a plurality of movable rods are provided spaced apart around a periphery of the movable ring; a first end of each of the plurality of movable rods is rotatably connected to the movable ring; a second end of each of the plurality of movable rods is rotatably connected to a first end of the movable plate; a second end of the movable plate is rotatably connected to the fixed ring; the movable ring is provided with a switch, and the switch is configured to lock a position of the movable ring on the connecting pipe.

In an embodiment, the switch is a solenoid valve; one part of the solenoid valve is located on the movable ring, and the other part of the solenoid valve is located on the connecting pipe; the movable ring is provided with a linear motor, and the linear motor is configured to drive movement of the movable ring.

In an embodiment, the solenoid valve and the linear motor are connected to a controller; the controller is connected to a power supply and a switch panel, and the switch panel is provided with buttons to control start and stop of the linear motor and opening and closing of the solenoid valve.

In an embodiment, the switch is an electric telescopic rod; a first end of the electric telescopic rod is connected to the movable ring, and a second end of the electric telescopic rod is connected to the fixed ring.

In an embodiment, a plurality of air-pressure buffer members are provided in the inlet pipe side by side.

In an embodiment, the movable ring comprises a first ring body and a second ring body; a plurality of elastic parts are provided between the first ring body and the second ring body; each of the plurality of movable rods is a V-shaped rod; two rod portions of the V-shaped rod are rotatably connected, and a rotatable connection end of the V-shaped rod is connected to the movable plate; two ends of the two rod portions of the V-shaped rod are rotatably connected to the first ring body or the second ring body.

In an embodiment, the movable ring is a spiral-shaped ring; the plurality of movable rods are distributed in a spiral form along an outer wall of the movable ring; and the first end of the movable plate is distributed in a spiral form.

This application further provides a noble gas isotope analysis device, comprising:

the buffer assembly;

wherein the noble gas isotope analysis device is a krypton (Kr) isotope analysis device; the Kr isotope analysis device comprises a valve V5 and a valve V9; the valve V5 is connected with a negative pressure device; and the valve V9 is connected with an isotope analyzer.

This application also provides a method for analyzing krypton (Kr) isotope in natural gas, comprising:

assembling the noble gas isotope analysis device;
removing water from a natural gas sample;
concentrating Xe component and Kr component in the natural gas sample;
separating the Kr component from the Xe component; and
transferring the Kr component to the isotope analyzer of the noble gas isotope analysis device for analysis.

Compared with the prior art, the present disclosure has the following beneficial effects.

The isotope analysis device provided herein can separate noble gas components from methane-rich natural gas and perform isotopic analysis on the noble gas components. The air-pressure buffer member is configured to buffer the air pressure changes to reduce the impact of natural gas samples on the pipeline near the V0 port.

The pneumatic components can be deformed under the action of a gas flow to slow down the gas flow. When the methane-rich natural gas in the external natural gas storage device enters the air inlet pipe under the action of negative pressure, i.e., under the action of wind, the pneumatic component is opened up and becomes larger in area, (namely, producing a resistance to the air flow like a kite), which can alleviate the impact of the natural gas on the air inlet pipe while allowing the natural gas to enter the air inlet pipe, thereby extending the service life of the air inlet pipe, and avoiding the leakage of natural gas.

A plurality of pneumatic components are provided spaced apart on the connecting pipe, and can form multi-layer resistance to the air flow, gradually alleviating the impact of the air flow on the natural gas on the wall of the inlet pipe, and diverting the pressure. In this way, the service life of the pneumatic components can also be extended.

In an embodiment, a plurality of air-pressure buffer members are provided in the air inlet pipe to form a multi-layer buffering effect against the impact of natural gas samples.

In an embodiment, in the pneumatic component, the movable ring is a spiral-shaped ring; the plurality of movable rods are distributed along an outer wall of the movable ring in a spiral form; when the air flow rushes toward the pneumatic component, it moves along the movable rod, and a tiny spiral air flow is formed, which effectively relieves the airflow impact.

In an embodiment, the use of the Kr isotope analysis device for Kr isotope analysis has a brilliant application prospect in the Kr isotopic tracing.

DETAILED DESCRIPTION OF EMBODIMENTS

Figure 1:
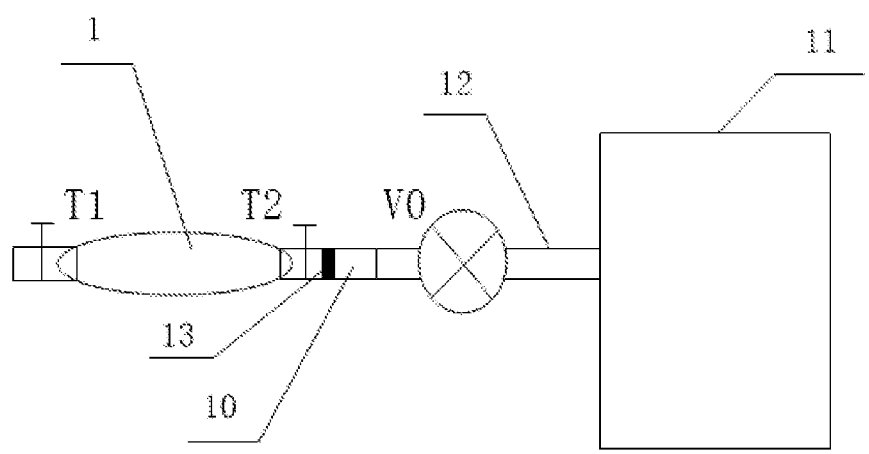
FIG. 1 is a schematic diagram of a noble gas isotope analysis device according to Embodiment 1 of this application.

This application will be described in detail below with reference to the embodiments and accompany drawings to enable those skilled in the art to better understand and implement the technical solutions of this application.

In the description of the present disclosure, unless otherwise specified, all reagents used are commercially available, and all methods used are common techniques in the art.

As used herein, it should be understood that orientation or position relationships indicated by terms such as "center", "longitudinal", "transverse", "length", "width", "thickness", "upper", "lower", "front", "back", "left", "right", "vertical", "horizontal", "top", "bottom", "inside", "outside", "clockwise", "counterclockwise", "axis", "radial", "circumferential", etc., are based on the orientations or position relationships shown in the drawings, and are used only for ease of describing the disclosure and simplifying the description, rather than indicating or implying that the referred apparatus or element must have a particular orientation or be constructed and operated in a particular orientation, and therefore, should not be construed as a limitation on the present disclosure. As used herein, the "upstream" and "downstream" are defined according to the gas flow direction from an external natural gas storage device 1 to an air inlet pipe 12.

As used herein the terms "first" and "second" are merely descriptive, and are not to be understood as indicating or implying relative importance or implicitly indicating the number of the indicated technical features. Therefore, a feature limited by "first" or "second" may expressly or impliedly include one or more of such features. In the description of the present disclosure, unless otherwise stated, "multiple" means two or more.

The noble gas isotope analysis device provided herein is an improvement made based on the device and method disclosed by Chinese patent No. 107167510B. Based on the principle of separating the krypton (Kr) component and xenon (Xe) component disclosed by the Chinese patent No. 107167510B, a buffer assembly that can buffer the air pressure change is introduced, which can alleviate the impact of natural gas samples on parts of the air inlet pipe 12 near the valve V0. Moreover, the Kr components can be separated for the isotopic analysis.

Embodiment 1

Referring to FIG. 1, a buffer assembly for a device for analyzing noble gas isotopes in natural gas is provided, where the noble gas isotope analysis device includes an isotope analysis device main body 11. The buffer assembly includes an air-pressure buffer member 10 and an air inlet pipe 12. The isotope analysis device main body 11 plays a role in separating noble gas components from methane-rich natural gas and performing isotopic analysis on the noble gas components. Reference can be made to the Chinese patent No. 107167510B for the structure of the isotope analysis device main body 11. The air inlet pipe 12 is connected to the isotope analysis device main body 11, and the air inlet pipe 12 is provided with a valve V0.

The air-pressure buffer member 10 is provided in the air inlet pipe 12. A first end of the air inlet pipe 12 is connected to the isotope analysis device main body 11, and a second end of the air inlet pipe 12 is connected to an external natural gas storage device 1. A first end of the external natural gas storage device 1 is provided with a valve T1, and a second end of the external natural gas storage device 1 is provided with a valve T2. The second end of the external natural gas storage device 1 is removably connected with the second end of the air inlet pipe 12. The valve T2 is connected with the air inlet pipe 12 through a connector 13. The joints of the valve T2, the air inlet pipe 12 and the connector 13 are sealed with a sealing sleeve or other materials to avoid the air leakage. The air inlet pipe 12 is provided with the valve V0. The air-pressure buffer member 10 is provided in the air inlet pipe 12, and located between the valve V0 and a mouth of the air inlet pipe 12. The air-pressure buffer member 10 is configured to buffer air pressure changes to reduce the impact of natural gas samples on the part of the air inlet pipe 12 near the port of the valve V0.

Figure 2:
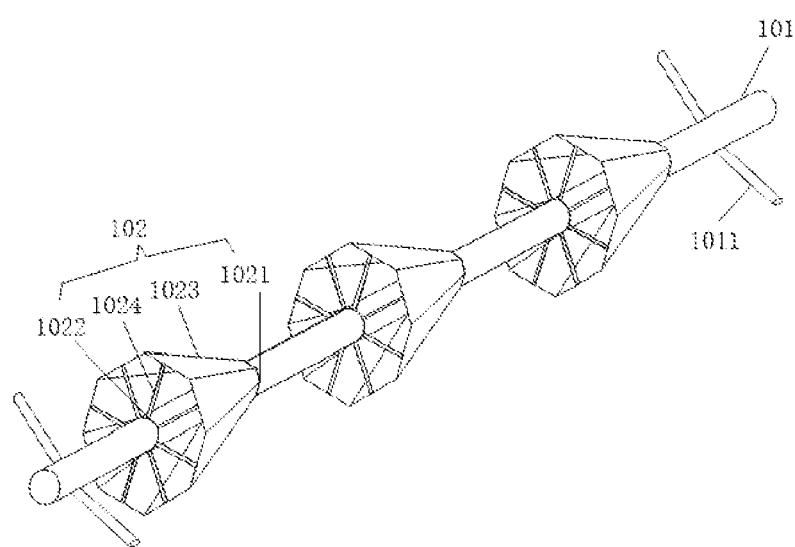
FIG. 2 is a schematic diagram of an air-pressure buffer member according to Embodiment 1 of this application.
Figure 3:
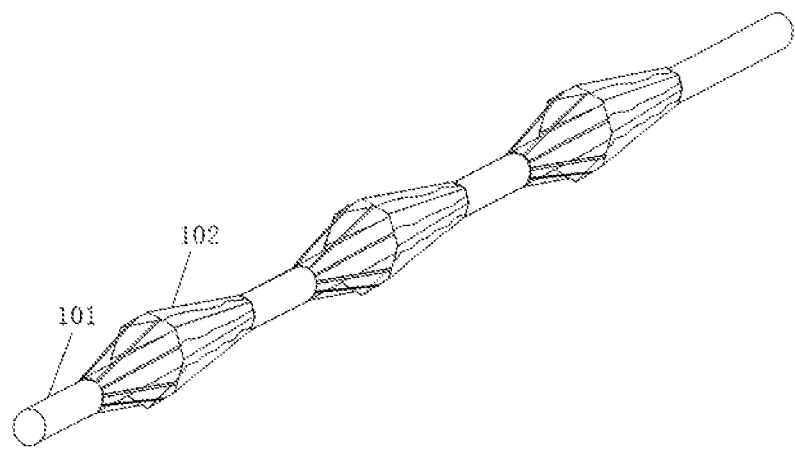
FIG. 3 is another schematic diagram of an air-pressure buffer member according to Embodiment 1 of this application.
Figure 4:
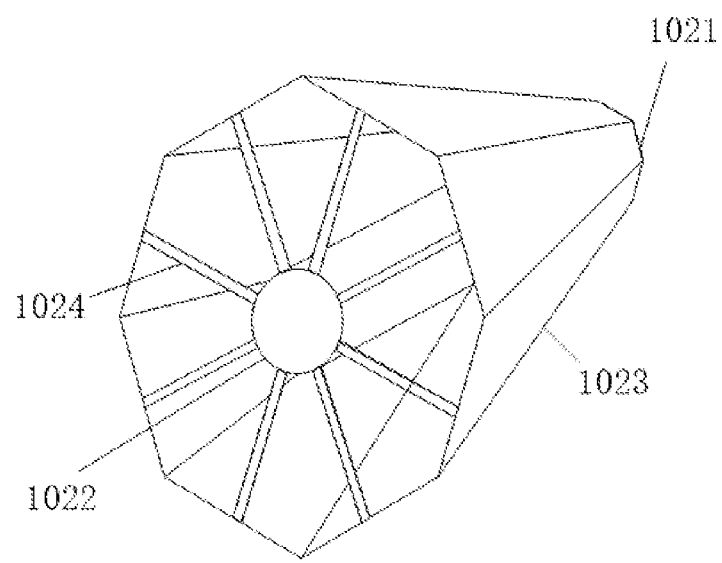
FIG. 4 is a schematic diagram of a pneumatic component according to Embodiment 1 of this application.

The structure of the air-pressure buffer member 10 is shown in FIGS. 2-4. The air-pressure buffer member 10 includes a connecting pipe 101, which is parallel to a center line of the air inlet pipe 12. A wall of the connecting pipe 101 is connected to a first end of the supporting rod 1011, and a second end of the supporting rod 1011 is connected to an inner wall of the air inlet pipe 12. A plurality of pneumatic components 102 are sleevedly provided outside the connecting pipe 101. The supporting rod is provided between the plurality of pneumatic components 102, or is provided on an upstream/downstream end of the connecting pipe 101.

The plurality of pneumatic components 102 are configured to be deformed under the action of a gas flow to slow down the gas flow. When the methane-rich natural gas in the external natural gas storage device 1 is fed to the air inlet pipe 12 under the action of negative pressure, i.e., under the action of wind, the pneumatic components 102 are spread out and become larger in area (namely, creating a resistance to the airflow like a kite), which can alleviate the impact of the natural gas on the air inlet pipe 12 while allowing the natural gas to enter the air inlet pipe 12, thereby extending the service life of the air inlet pipe 12, and avoiding the leakage of natural gas. The multiple pneumatic components 102 are provided spaced apart on the connecting pipe 101, and can form multi-layer resistance to the airflow, gradually alleviating the impact of the air flow on the natural gas on the wall of the air inlet pipe 12, and diverting the pressure. In this way, the service life of the pneumatic components 102 can also be extended.

Each pneumatic component 102 includes a fixed ring 1021, a movable ring 1022, a movable plate 1023 and a plurality of movable rods 1024. The fixed ring 1021 is fixedly provided on the connecting pipe 101. The movable ring 1022 is provided upstream of the fixed ring 1021, that is, in the pneumatic component 102, the movable ring 1022 is arranged closer to the external natural gas storage device 1 than the fixed ring 1021. The movable ring 1022 is sleevedly provided outside the connecting pipe 101, and is able to reciprocate along a length direction of the connecting pipe 101. The plurality of movable rods 1024 are provided spaced apart around a periphery of the movable ring 1022. A first end of each of the plurality of movable rods 1024 is hinged with the movable ring 1022. A second end of each of the plurality of movable rods 1024 is hinged with a first end of the movable plate 1023. It should be noted that the plurality of movable rods 1024 are in one-to-one correspondence with the movable plate 1023. A second end of the movable plate 1023 is rotatably connected to the fixed ring 1021. In general, the movable rods 1024 and the movable plates 1023 are distributed in a circular array around the connecting pipe 101. The movable plate 1023 is provided with two rigid bars, and a flexible cloth is connected between the two rigid bars. The movable rod 1024 is connected to the flexible cloth. Or, the two rigid bars of the movable plate 1023 are each connected with an end of the movable rod 1024, and the other end of the movable rod 1024 is connected with the movable ring 1022.

When the natural gas flows from the external natural gas storage device 1 to the air inlet pipe 12, an impact force is generated on the movable plates 1023. The movable ring 1022 moves as far as possible toward the corresponding fixed ring 1021, so that the multiple movable plates 1023 are spread just like "unfolding an umbrella", forming a state as shown in FIG. 2.

The movable ring 1022 is provided with a switch, which is connected with the movable ring 1022 and the connecting pipe 101. When it is not required to perform sampling from the external natural gas storage device 1, the movable ring 1022 is located at a position closest to the external natural gas storage device 1. The position of the movable ring 1022 on the connecting pipe 101 is locked by the switch, so that all the movable plates 1023 begin to become folded just like "folding an umbrella", forming a state as shown in FIG. 3.

In this embodiment, the switch is a solenoid valve. One part of the solenoid valve is located on the movable ring 1022, and the other part is located on the connecting pipe 101. The movable ring 1022 is provided with a linear motor, which is configured to control the movable ring 1022 to reciprocate along the length direction of the connecting pipe 101. When the linear motor is turned on, the movable ring 1022 is controlled to move in a direction close to the external natural gas storage device 1, and two parts of the solenoid valve are assembled. When the solenoid valve is closed, the position of the movable ring 1022 is locked on the connecting pipe 101.

When it needs to take a sample from the external natural gas storage device 1, the solenoid valve is switched on, and the two parts of the solenoid valve are separable, and when the negative pressure is created in the air inlet pipe 12 in advance, after the valve T2 is opened, the switch of the linear motor is operated to allow the linear motor to move in the direction away from the natural gas storage device 1. In this case, the natural gas is fed into the air inlet pipe 12 to separate the two parts of the solenoid valve, and the movable ring 1022 moves toward the corresponding fixed ring 1021.

Considering that the solenoid valve has a minimum operating temperature of about −290° C., and the liquefaction temperature of Kr gas is higher than −290° C., the solenoid valve selected in this embodiment can meet the low-temperature operation.

In order to facilitate control, the solenoid valve and the linear motor are both connected to a controller, such as a PLC (Programmable Logic Controller). The controller is connected with a power supply and a switch panel, and the switch panel is provided with buttons to control the opening and closing of the solenoid valve and the start and stop of the linear motor.

Embodiment 2

Figure 5:
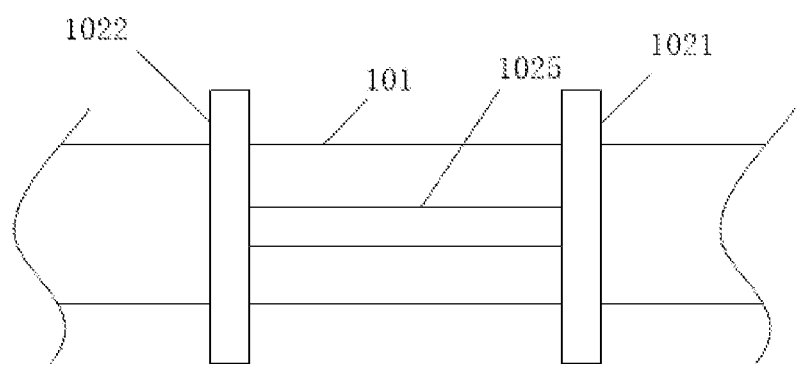
FIG. 5 schematically shows connection of a switch, a movable ring and a fixed ring according to Embodiment 2 of this application.

A buffer assembly compatible with a device for analyzing noble gas isotopes in natural gas is provided herein, which is basically the same as that of Embodiment 1 in structure except the switch structure (as shown in FIG. 5).

The switch is an electric telescopic rod 1025. A first end of the electric telescopic rod 1025 is connected to the movable ring 1022, and a second end of the electric telescopic rod 1025 is connected to the fixed ring 1021.

When it is required to perform sampling from the external natural gas storage device 1, the electric telescopic rod 1025 is switched on to drive the movable ring 1022 to move in the direction close to the external natural gas storage device 1. The position of the movable ring 1022 on the connecting pipe 101 is locked by the electric telescopic rod 1025, so that the movable plates 1023 are folded like a closed umbrella, as shown in FIG. 3.

When it needs to take a sample from the external natural gas storage device 1, a negative pressure is created in the air inlet pipe 12 in advance with, and then the electric telescopic rod 1025 is retracted while the valve T2 is opened. The natural gas enters into the air inlet pipe 12, and the movable ring 1022 is moved toward the corresponding fixed ring 1021, generating a buffering resistance to the gas flow.

Embodiment 3

Figure 6:
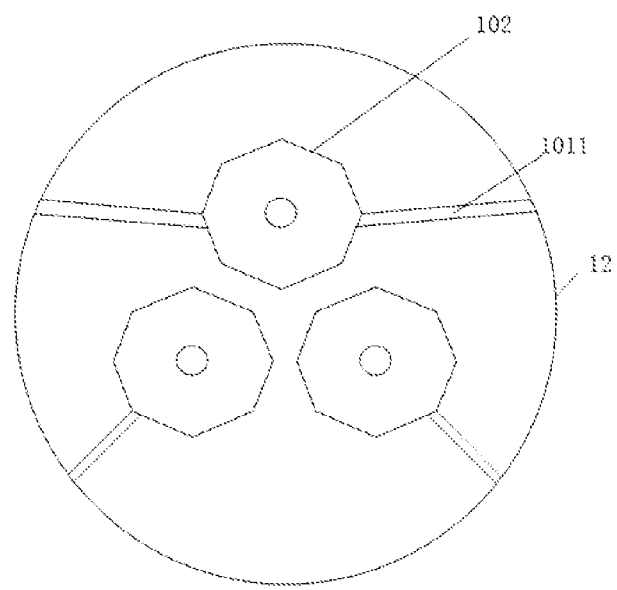
FIG. 6 is a longitudinal sectional view of the internal structure of the air inlet pipe in accordance with Embodiment 3 of this application.

A buffer assembly compatible with a device for analyzing noble gas isotopes in natural gas is provided, which is basically the same as that of Embodiment 1 in structure. The difference between Embodiments 1 and 3 is that a plurality of air-pressure buffer members 10 are provided in the air inlet pipe 12, and are distributed side by side in a circular array within the air inlet pipe 12 (referring to FIG. 6), thereby forming multi-layer buffering for the impact brought by the natural gas samples.

Embodiment 4

Figure 7:
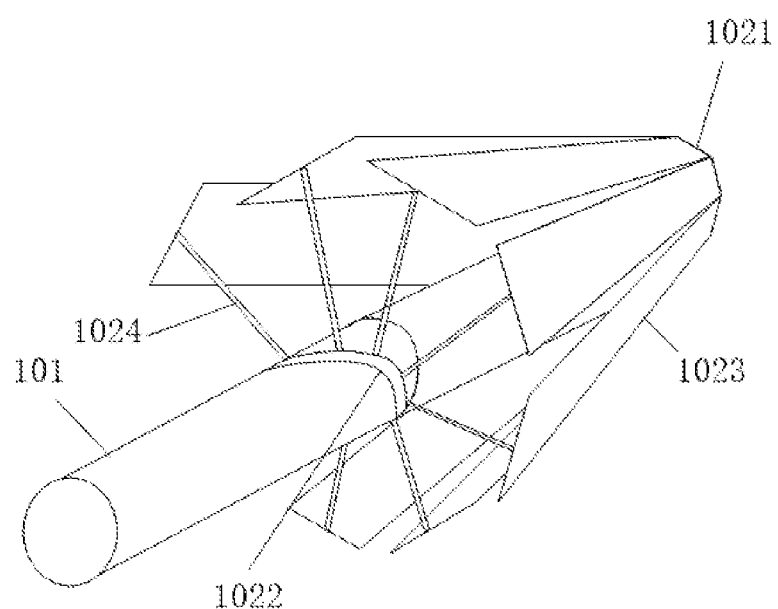
FIG. 7 schematically shows connection of the pneumatic components and a connecting pipe according to Embodiment 4 of this application.

A buffer assembly compatible with a device for analyzing noble gas isotopes in natural gas is provided, which is basically the same as that of Embodiment 1 in structure except the following differences. Referring to FIG. 7, in the same pneumatic component 102, the movable ring 1022 is a spiral-shaped ring, and the plurality of movable rods 1024 are distributed in a spiral shape around an outer wall of the movable ring 1022, and the ends of the movable plates 1023 connected to the movable rod 1024 are also distributed in a spiral shape. When the air flow rushes towards the pneumatic component 102, it moves along the movable rod 1024 to form a tiny spiral air flow, which can effectively alleviate the impact of the air flow.

Figure 8:
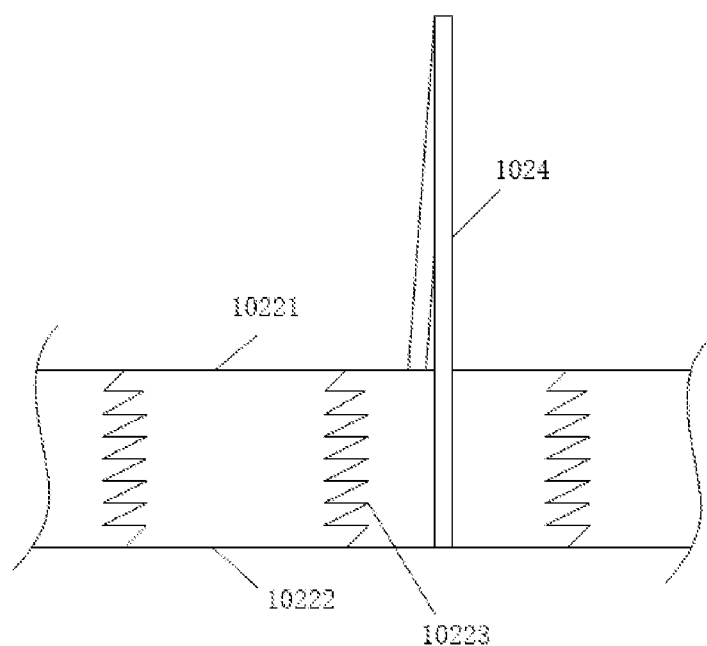
FIG. 8 schematically shows connection of a movable ring and movable rods according to Embodiment 4 of this application.
Figure 9:
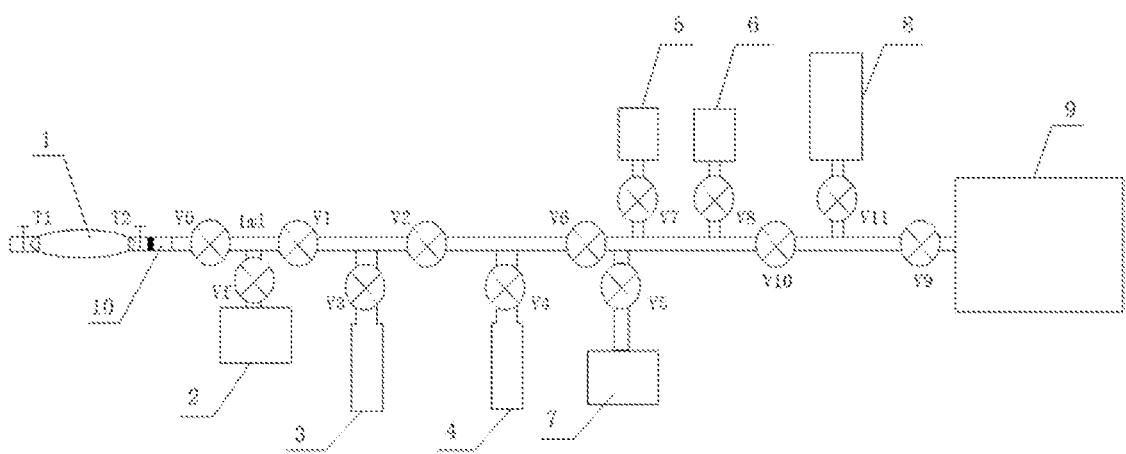
FIG. 9 is a schematic diagram of a krypton (Kr) isotope analysis device according to Embodiment 5 of this application.

In an embodiment, with reference to FIG. 8, the movable ring 1022 includes a first ring body 10221 and a second ring body 10222. The first ring body 10221 and the second ring body 10222 have the same size and shape. There are multiple elastic components (e.g., springs 10223) arranged between the first ring body 10221 and the second ring body 10222. The movable rod 1024 is a V-shaped rod. The two rod portions of the V-shaped rod are hinged together, and the hinge end is connected to the corresponding movable plate 1023. One free end of the V-shaped rod is connected to the first ring body 10221, and the other free end of the V-shaped rod is connected to the second ring body 10222. When the air flow hits the movable plate 1023, the displacement of the first ring body 10221 and the second ring body 10222 is buffered by the spring 10223, which can also decelerate the airflow.

Embodiment 5

A device for analyzing Kr isotopes in methane-rich natural gas is provided herein, which includes a Kr isotope analysis device main body and an air-pressure buffer member 10. The structure of the Kr isotope analysis device main body is designed with reference to the Chinese patent No. 107167510B, including a negative pressure device 2, a water absorption device 3, a collection device 4, a reactive adsorption device 5, a filter device 6, a negative pressure device 7, a separation device 8, an isotope analyzer 9, valve V1, valve V2, valve V3, valve V4, valve V5, valve V6, valve V7, valve V8, valve V9, valve V10, valve V11, and valve Vf. The air-pressure buffer member 10 is provided in the air inlet pipe 12. A first end of the air inlet pipe 12 is connected to the Kr isotope analysis device main body, and a second end of the air inlet pipe 12 is connected to an external natural gas storage device 1. A first end of the external natural gas storage device 1 is provided with a valve T1, and a second end of the external natural gas storage device 1 is provided with a valve T2. The second end of the external natural gas storage device 1 is removably connected with the second end of the air inlet pipe 12. The valve T2 is connected to the air inlet pipe 12 through a connector 13. The air inlet pipe 12 is provided with a valve V0, and the air-pressure buffer member 10 is provided between the valve V0 and the valve T2.

The valve V0, valve V1, valve V2, valve V3, valve V4, valve V5, valve V6, valve V7, valve V8, valve V9, valve V10, valve V11, valve Vf, valve T1, valve T2, negative pressure device 2, water absorption device 3, collection device 4, reactive adsorption device 5, filter device 6, negative pressure device 7, separation device 8, isotope analyzer 9 and external natural gas storage device 1 are all connected with reference to FIG. 1 of the Chinese patent No. 107167510B.

The isotope analysis device disclosed by the Chinese patent No. 107167510B is designed for analyzing the Xe isotope components, and the present disclosure is used for analyzing the Kr isotope components, as shown in FIG. 8.

In the present disclosure, the valve V5 is connected to the negative pressure device 7, and the valve V9 is not connected to the negative pressure device 7. In the present disclosure, the valve V9 is connected to the isotope analyzer 9.

The Kr isotopes are analyzed as follows.

(S1) The high-pressure cylinder for collecting/storing natural gas samples is connected to the valve V0, and the valve V0 and the valve Vf are opened. The air inlet pipe 12 was vacuumized to $10^{-5}$ Pa.

(S2) The valve Vf was closed, and the valve T2 was opened and held for 20 s. At this time, the air-pressure buffer member 10 plays a role in buffering the resistance to alleviate the impact of the gas flow on the air inlet pipe 12.

(S3) The valve V0 is closed and 1 mL of a natural gas sample is taken between the valve V0 and the valve V1.

(S4) The temperature at the valve V3 is reduced and maintained at the temperature of an alcohol-liquid nitrogen mixture, and the valve V1 and the valve V3 are opened and held for 2 min to remove water from the sample.

(S5) The valves V3 and V1 are closed, and the valves V2 and V4 are opened and held for 2 min. Kr and Xe components are concentrated by cold-processing at the temperature of liquid nitrogen at the valve V4.

(S6) The valve V4 is closed, and the valves Vf and V1 are opened to allow the remaining sample to be pumped out until the vacuum degree returns to $10^{-5}$ Pa.

(S7) A second sampling is performed. The valves V1, V2 and Vf are closed, and the valve V0 is opened and held for 20 s; and steps (S3)-(S6) are repeated.

(S8) The step (S7) (i.e., the second sampling) is repeated 10-15 times to enable the enrichment of Kr and Xe components in natural gas samples.

(S9) The valve V2 is closed, and the valve V4 is opened, heated to 100° C. to release the collected Kr and Xe components.

(S10) The valve V5 is closed, and the valve V6 is opened. A titanium sponge furnace is heated up to 800° C. and held for 10 min to further remove reactive gases remaining in the sample, and at the same time, a getter pump is operated to remove the $H_2$ from the sample.

(S11) The valve V9 is closed, and the valves V10 and V11 are opened. Temperature of a cryogenic pump is decreased to 140 K and held for 10 min to collect the Xe component.

(S12) The valve V11 is closed and the valve V9 is opened to feed the Kr component into the noble gas mass spectrometer for the analysis of Kr isotopes.

It should be noted that unless otherwise specified, the connection between components is performed using a method in the prior art, and is thus not described in detail herein.

Regarding the numerical range disclosed herein, it should be understood that the two endpoints and any numerical value therebetween are practicable. Since the embodiments all share the same step and process, this application merely presents some preferred embodiments to avoid redundancy. Although the present disclosure has been described in detail above with reference to the preferred embodiments, those skilled in the art can still make various changes and modifications to these embodiments. It should be noted that those changes and modifications made without departing from the spirit of the disclosure shall fall within the scope of the disclosure defined by the appended claims.

What is claimed is:

1. A buffer assembly for a noble gas isotope analysis device, comprising: an air inlet pipe; and an air-pressure buffer member; wherein the air inlet pipe is connected to the noble gas isotope analysis device; the air inlet pipe is provided with a first valve; and the air-pressure buffer member is arranged in the air inlet pipe; the air-pressure buffer member comprises a connecting pipe; the connecting pipe is provided in the air inlet pipe; a plurality of pneumatic components are sleevedly provided outside the connecting pipe; and the plurality of pneumatic components are configured to slow down a gas flow; each of the plurality of pneumatic components comprises a fixed ring; the fixed ring is fixedly provided on the connecting pipe; a movable ring is provided upstream of the fixed ring; the movable ring is movably sleeved outside the connecting pipe; a plurality of movable rods are provided spaced apart around a periphery of the movable ring; a first end of each of the plurality of movable rods is rotatably connected to the movable ring; a second end of each of the plurality of movable rods is rotatably connected to a first end of a movable plate; a second end of the movable plate is rotatably connected to the fixed ring; the movable ring is provided with a switch, and the switch is configured to lock a position of the movable ring on the connecting pipe; the movable ring comprises a first ring body and a second ring body; a plurality of elastic parts are provided between the first ring body and the second ring body; each of the plurality of movable rods is a V-shaped rod; two rod portions of the V-shaped rod are rotatably connected, and a rotatable connection end of the V-shaped rod is connected to the movable plate; two ends of the two rod portions of the V-shaped rod are rotatably connected to the first ring body or the second ring body; the movable ring is a spiral-shaped ring; the plurality of movable rods are distributed along a circumferential direction of the movable ring; and the first end of the movable plate is distributed in a spiral form; and the switch is a solenoid valve; one part of the solenoid valve is located on the movable ring, and the other part of the solenoid valve is located on the connecting pipe; the movable ring is provided with a linear motor, and the linear motor is configured to drive movement of the movable ring; the solenoid valve and the linear motor are connected to a controller; the controller is connected to a power supply and a switch panel, and the switch panel is provided with buttons configured to control start and stop of the linear motor and opening and closing of the solenoid valve; or the switch is an electric telescopic rod; a first end of the electric telescopic rod is connected to the movable ring, and a second end of the electric telescopic rod is connected to the fixed ring.

2. The buffer assembly of claim 1, wherein the connecting pipe is connected with an inner wall of the air inlet pipe through a supporting rod.

3. A noble gas isotope analysis device, comprising:
the buffer assembly of claim 1;
wherein the noble gas isotope analysis device is a krypton (Kr) isotope analysis device; the Kr isotope analysis device comprises a second valve and a third valve; the second valve is connected with a negative pressure device; and the third valve is connected with an isotope analyzer.

4. A method for analyzing krypton (Kr) isotope in natural gas, comprising:
assembling the noble gas isotope analysis device of claim 3;
removing water from a natural gas sample;
concentrating Xe component and Kr component in the natural gas sample;
separating the Kr component from the Xe component; and
transferring the Kr component to the isotope analyzer of the noble gas isotope analysis device for analysis.

* * * * *